United States Patent [19]

Kristiansen et al.

[11] Patent Number: 4,623,642

[45] Date of Patent: * Nov. 18, 1986

[54] NOVEL N-PHOSPHORYL- OR N-THIOPHOSPHORYL-N'S-TRIAZINYL-FORMAMIDINES

[75] Inventors: Odd Kristiansen, Möhlin; Jozef Drabek, Oberwil; Victor Flück, Binningen, all of Switzerland

[73] Assignee: Ciba-Geigy Corporation, Ardsley, N.Y.

[*] Notice: The portion of the term of this patent subsequent to Sep. 3, 2002 has been disclaimed.

[21] Appl. No.: 808,225

[22] Filed: Dec. 12, 1985

Related U.S. Application Data

[63] Continuation of Ser. No. 690,790, Jan., 1985, abandoned.

[30] Foreign Application Priority Data

Jan. 20, 1984 [CH] Switzerland ............... 247/84
Jan. 20, 1984 [CH] Switzerland ............... 248/84
Nov. 30, 1984 [CH] Switzerland ............... 5712/84

[51] Int. Cl.$^4$ .................. C07D 251/70; A01N 43/68; A01N 59/26; C07F 0/65
[52] U.S. Cl. ........................ 514/84; 544/195
[58] Field of Search ............... 514/84; 544/195

[56] References Cited

U.S. PATENT DOCUMENTS 3,989,702 11/1976 Garner ................ 544/195
4,539,314 9/1985 Kristiansen et al. ........ 514/84

FOREIGN PATENT DOCUMENTS 1055336 1/1967 United Kingdom ................ 544/195

OTHER PUBLICATIONS

Melnikev, Chemical Abstracts, vol. 95, entry 110188m (1981).
Melnikev, Chemical Abstracts, vol. 95, entry 92368p (1981).

*Primary Examiner*—John M. Ford
*Attorney, Agent, or Firm*—Edward McC. Roberts; Kevin T. Mansfield

[57] ABSTRACT

N-phosphoryl- or N-thiophosphoryl-N'-s-triazinylformamidines of the formula

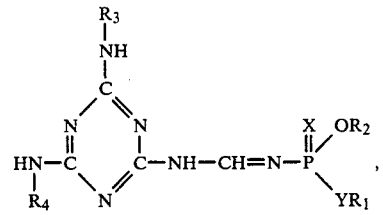

wherein $R_1$ and $R_2$ independently of one another are each $C_1$–$C_{20}$-alkyl, or phenyl unsubstituted or substituted by halogen atoms, $R_3$ is $C_1$–$C_6$-alkyl or $C_3$–$C_6$-cycloalkyl, $R_4$ is hydrogen, $C_1$–$C_6$-alkyl or $C_3$–$C_6$-cycloalkyl, and X and Y are each oxygen or sulfur.

A process for producing these triazines and their use for controlling pests are described.

10 Claims, No Drawings

NOVEL N-PHOSPHORYL- OR N-THIOPHOSPHORYL-N'-S-TRIAZINYL-FORMAMIDINES

This application is a continuation of application Ser. No. 690,790, filed Jan. 11, 1985, now abandoned.

The present invention relates to N-phosphoryl- or N-thiophosphoryl-N'-s-triazinyl-formamidines, to processes for producing them, and to their use for controlling pests.

The N-phosphoryl- or N-thiophosphoryl-N'-s-triazinylformamidines have the formula I

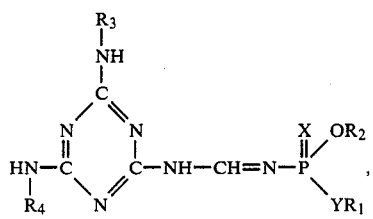

wherein
$R_1$ and $R_2$ independently of one another are each $C_1$–$C_{20}$-alkyl, or phenyl unsubstituted or substituted by halogen atoms,
$R_3$ is $C_1$–$C_6$-alkyl, or $C_3$–$C_6$-cycloalkyl,
$R_4$ is hydrogen, $C_1$–$C_6$-alkyl or $C_3$–$C_6$-cycloalkyl, and
X and Y are each oxygen or sulfur.

The compounds of the formula I can also be in their tautomeric form.

By halogen is meant in this case fluorine, chlorine, bromine or iodine.

The alkyl groups denoted by $R_1$, $R_2$, $R_3$ and $R_4$ can be straight-chain or branched-chain. In the case of $R_1$ and $R_2$, they have in the chain preferably 1 to 6, especially however 1 to 4, carbon atoms. Examples of such groups are, inter alia, methyl, ethyl, propyl, isopropyl, n-butyl, n-pentyl, n-hexyl, and isomers thereof.

The preferred cycloalkyl group denoted by $R_3$ and $R_4$ is cyclopropyl.

Preferred compounds of the formula I are those wherein
$R_1$ is $C_1$–$C_6$-alkyl,
$R_2$ is $C_1$–$C_6$-alkyl, or phenyl unsubstituted or substituted by one to three halogen atoms,
$R_3$ is cyclopropyl,
$R_4$ is hydrogen, isopropyl or cyclopropyl, and
X and Y are each oxygen or sulfur; or wherein
$R_1$ and $R_3$ independently of one another are each $C_1$–$C_6$-alkyl,
$R_2$ is $C_1$–$C_6$-alkyl, or phenyl unsubstituted or substituted by one to three halogen atoms,
$R_4$ is hydrogen, and
X and Y are each oxygen or sulfur.

Particularly preferred compounds of the formula I are those wherein
$R_1$ and $R_2$ independently of one another are each $C_1$–$C_4$-alkyl,
$R_3$ is cyclopropyl,
$R_4$ is hydrogen or cyclopropyl, and
X and Y are each oxygen or sulfur; or wherein
$R_1$, $R_2$ and $R_3$ independently of one another are each $C_1$–$C_4$-alkyl,
$R_4$ is hydrogen, and
X and Y are each oxygen or sulfur.

The compounds of the formula I can be produced by methods known per se, for example as follows:

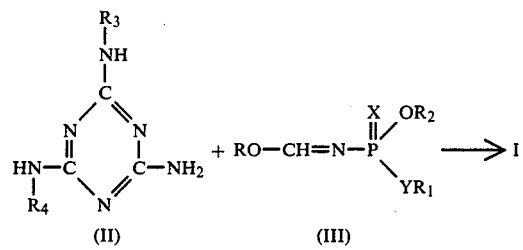

In the formulae II and III, the symbols $R_1$–$R_4$, X and Y have the meanings defined for the formula I, and R is $C_1$–$C_6$-alkyl, especially methyl or ethyl.

The process is performed at a reaction temperature of between 50° C. and 130° C., preferably between 80° C. and 120° C., under normal or slightly elevated pressure, and optionally in the presence of a solvent or diluent inert to the reactants.

Suitable solvents or diluents are for example: aliphatic and aromatic hydrocarbons, particularly benzene, toluene or xylenes; and ketones, such as acetone, methyl ethyl ketone and cyclohexanone, or ethers, such as dioxane.

The starting materials of the formulae II and III are known, or they can be produced by methods analogous to known methods.

The compounds of the formula I are suitable for controlling pests on animals and plants and in the soil. They are particularly suitable for controlling insects, for example of the orders: Lepidoptera, Coleoptera, Homoptera, Heteroptera, Diptera, Thysanoptera, Orthoptera, Anoplura Siphonaptera, Mallophaga, Thysanura, Isoptera, Psocoptera and Hymenoptera, and also phytopathogenic mites and ticks of the order Acarina.

Compounds of the formula I are suitable in particular for controlling insects that damage plants, especially insects that damage plants by eating, in crops of ornamental plants and productive plants, particularly in cotton and rice crops (for example against *Spodoptera littoralis, Heliothis virescens* and *Nilaparvata lugens*), and in vegetable crops (for example against *Leptinotarsa decemlineata* and *Myzus persicae*), and also for controlling soil insects (for example: *Aulacophora femoralis, Chortophila brassicae, Diabrotica balteata, Pachnoda savigni* and *Scotia ypsilon*).

It is to be emphasised in this connection that the stated compounds also exhibit a pronounced systemic action.

Active substances of the formula I have a very favourable action also against flies, for example *Musca domestica,* and against mosquito larvae. Furthermore, they are distinguished by a broad ovicidal and ovilarvicidal action, and have also a valuable action against ectoparasitic mites and ticks, for example of the families: Ixodidae, Argasidae and Dermanyssidae. The compounds of the formula I have moreover good nematocidal properties.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I amd optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Depending on the nature of the active ingredient of the formula I to be formulated, suitable surface-active compounds are: nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included amongst these are also the salts of sulfuric acid esters and of sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylenepolyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1982; and Dr. Helmut Stache "Tensid Taschenbuch", Carl Hanser Verlag, Munich/Vienna, 1981.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25%, of a tenside.

Whereas commercial products are preferably in the form of concentrated compositions, the preparations employed by the end-user are as a rule diluted.

The compositions can also contain further additives, such as stabilisers, antifoam agents, viscosity regulators, binders and adhesives, as well as fertilisers or other active ingredients for obtaining special effects.

Formulation examples for liquid active ingredients of the formula I (%=percent by weight)

| Emulsion concentrates | (a) | (b) | (c) |
|---|---|---|---|
| active ingredient of the formula I | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol | — | 12% | 4% |

| Emulsion concentrates | (a) | (b) | (c) |
|---|---|---|---|
| ether (30 mols of ethylene oxide) | | | |
| cyclohexanone | — | 15% | 20% |
| xylene mixture | 65% | 25% | 20% |

Emulsions of any required concentration can be produced from concentrates of this type by dilution with water.

| Solutions | (a) | (b) | (c) | (d) |
|---|---|---|---|---|
| active ingredient of the formula I | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

These solutions are suitable for application in the form of very small drops.

| Granulates | (a) | (b) |
|---|---|---|
| active ingredient of the formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| Dusts | (a) | (b) |
|---|---|---|
| active ingredient of the formula I | 2% | 5% |
| highly dispersed silicic acid | 1% | 5% |
| talcum | 97% | — |
| kaolin | — | 90% |

Dusts ready for use are obtained by the intimate mixing together of the carriers with the active ingredient.

Formulation examples for solid active ingredients of the formula I (%=percent by weight)

| Wettable powders | (a) | (b) | (c) |
|---|---|---|---|
| active ingredient of the formula I | 25% | 50% | 75% |
| sodium lignin sulfonate | 5% | 5% | — |
| sodium laurylsulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| Emulsion concentrate | |
|---|---|
| active ingredient of the formula I | 10% |
| octylphenol polyethylene glycol ether (4-5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| Dusts | (a) | (b) |
|---|---|---|
| active ingredient of the formula I | 5% | 8% |
| talcum | 95% | — |
| kaolin | — | 92% |

Dusts ready for use are obtained by mixing the active ingredient with the carrier, and grinding the mixture in a suitable mill.

| Extruder granulate | |
|---|---|
| active ingredient of the formula I | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded and then dried in a stream of air.

| Coated granulate | |
|---|---|
| active ingredient of the formula I | 3% |
| polyethylene glycol (M.W. 200) | 3% |
| kaolin | 94% |
| (M.W. = molecular weight) | |

The finely ground active ingredient is evenly applied, in a mixer, to the kaolin moistened with polyethylene glycol. Dustfree coated granulates are obtained in this manner.

| Suspension concentrate | |
|---|---|
| active ingredient of the formula I | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

EXAMPLE 1

Production of the Compound of the Formula

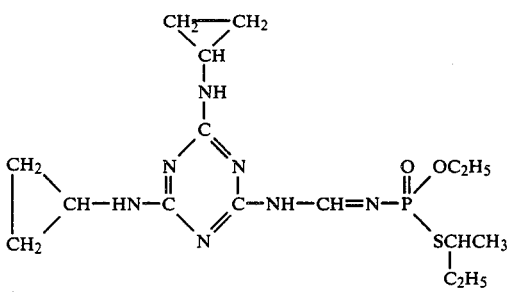
No. 1

A solution of 10.3 g of 2-amino-4,6-bis-cyclopropylamino-1,3,5-triazine and 18.75 g of N-(O-ethyl-S-sec-butylthiolophosphoryl)iminoformic acid ethyl ester in 200 ml of dioxane is refluxed for 10 hours. After removal of the solvent by distillation, the crude product is taken up in chloroform and extracted by shaking with water. Removal by distillation of the chloroform and chromatographical purification (silica gel; eluant: 90% chloroform, 10% ethanol) yield the title compound, m.p. 168°–169° C.

The following compounds are produced in an analogous manner:

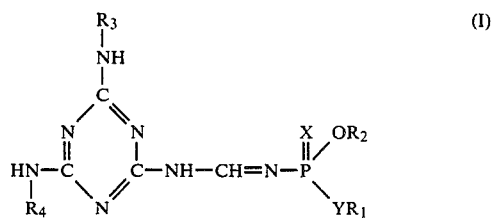
(I)

| No. | $R_1$ | $R_2$ | $R_3$ | $R_4$ | X | Y | Physical data |
|---|---|---|---|---|---|---|---|
| 2 | $C_3H_{7(n)}$ | $C_2H_5$ | cyclopropyl | $C_3H_{7(i)}$ | O | S | m.p.: 171–173° C. |
| 3 | $CH_3$ | $CH_3$ | cyclopropyl | $C_3H_{7(i)}$ | O | S | amorphous |
| 4 | $C_3H_{7(n)}$ | $C_2H_5$ | cyclopropyl | cyclopropyl | O | S | m.p.: 133–136° C. |
| 5 | $C_2H_5$ | $C_2H_5$ | cyclopropyl | cyclopropyl | O | S | m.p.: 147–150° C. |
| 6 | $C_4H_9$ (sec.) | $C_2H_5$ | cyclopropyl | $C_3H_{7(i)}$ | O | S | m.p.: 197–199° C. |
| 7 | $CH_3$ | $CH_3$ | $C_3H_{7(i)}$ | H | O | S | m.p.: 160–162° C. |
| 8 | $C_3H_{7(n)}$ | $C_2H_5$ | $C_3H_{7(i)}$ | H | O | S | m.p.: 182–184° C. |
| 9 | $C_3H_{7(n)}$ | $C_2H_5$ | $CH_3$ | H | O | S | m.p.: 191–193° C. |
| 10 | $C_2H_5$ | $C_2H_5$ | $C_3H_{7(i)}$ | H | O | S | m.p.: 192–195° C. |

EXAMPLE 2

Insecticidal Stomach-Poison Action

Cotton plants are sprayed with a test solution containing 100 ppm of the compound to be tested. After the drying of the coating, larvae of Spodoptera littoralis (L-1) are settled onto the cotton plants. The test is carried out at 24° C. with 60% relative humidity.

Compounds according to Example 1 have in the above test a 100% stomach-poison action against Spodoptera larvae.

EXAMPLE 3

Action Against *Diabrotica balteata*

750 ml of compost soil are mixed with 150 ml of a test solution containing 3 ppm of active ingredient. Maize seedlings are potted with the treated soil in plastic pots (4 seedlings per pot of 10 cm diameter). The pots are immediately afterwards infested with 10 $L_3$ larvae of Diabrotica balteata. An evaluation of the results achieved is made 10 days after infestation with the larvae.

Compounds according to Example 1 are 100% effective in the above test against $L_3$ larvae of *Diabrotica balteata*.

What is claimed is:

1. An N-phosphoryl- or N-thiophosphoryl-N'-s-triazinyl-formamidine of the formula I

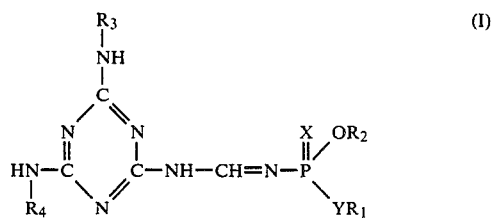
(I)

wherein
$R_1$ and $R_2$ independently of one another are each $C_1$–$C_{20}$-alkyl, or phenyl unsubstituted or substituted by halogen atoms,
$R_3$ is $C_1$–$C_6$-alkyl,
$R_4$ is hydrogen, $C_1$–$C_6$-alkyl or $C_3$–$C_6$-cycloalkyl, or
$R_3$ is $C_3$–$C_6$-cycloalkyl and
$R_4$ is $C_1$–$C_6$-alkyl or $C_3$–$C_6$-cycloalkyl, and
X and Y are each oxygen or sulfur.
2. A compound according to claim 1, wherein
$R_1$ is $C_1$–$C_6$-alkyl,
$R_2$ is $C_1$–$C_6$-alkyl, or phenyl unsubstituted or substituted by one to three halogen atoms,
$R_3$ is cyclopropyl,
$R_4$ is isopropyl or cyclopropyl, and
X and Y are each oxygen or sulfur.
3. A compound according to claim 2, wherein
$R_1$ and $R_2$ independently of one another are each $C_1$–$C_4$-alkyl,
$R_3$ is cyclopropyl,
$R_4$ is cyclopropyl, and
X and Y are each oxygen or sulfur.
4. A compound according to claim 1, wherein
$R_1$ and $R_3$ independently of one another are each $C_1$–$C_6$-alkyl,
$R_2$ is $C_1$–$C_6$-alkyl, or phenyl unsubstituted or substituted by one to three halogen atoms,
$R_4$ is hydrogen, and
X and Y are each oxygen or sulfur.
5. A compound according to claim 4, wherein
$R_1$, $R_2$ and $R_3$ independently of one another are each $C_1$–$C_4$-alkyl,
$R_4$ is hydrogen, and
X and Y are each oxygen or sulfur.
6. The compound according to claim 3 of the formula 7. The compound according to claim 5 of the formula

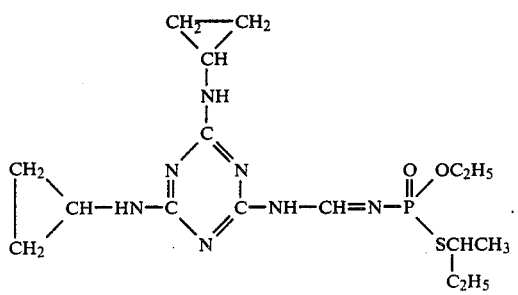

8. The compound according to claim 5 of the formula

9. A composition for controlling insects, pathogenic mites and ticks of the order acarina which contains a compound according to claim 1 as an active ingredient.

10. A method of controlling insects, phytopathogenic mites and ticks of the order acarina on animals and plants and in the soil, which method comprises applying thereto or to the locus thereof an effective amount of a compound according to claim 1.